United States Patent [19]

Dubois

[11] Patent Number: 5,736,654
[45] Date of Patent: Apr. 7, 1998

[54] SELF-CONTAINED ON-LINE SAMPLING APPARATUS

[75] Inventor: Robert N. Dubois, Sherwood Park, Canada

[73] Assignee: The Dow Chemical Company, Midland, Mich.

[21] Appl. No.: 751,009

[22] Filed: Nov. 15, 1996

Related U.S. Application Data

[60] Provisional application No. 60/074,476, Nov. 22, 1995.

[51] Int. Cl.⁶ ................................................. G01N 1/14
[52] U.S. Cl. ................................................. 73/863.84
[58] Field of Search .................... 73/863.01, 863.11, 73/863.23–863.25, 863.73, 863.81, 863.84, 863.83, 863.86, 864.34, 864.35, 864.73, 864.74, 864.81, 61, 59, 23.41, 23.42, 61.55, 61.56, 61.61

[56] References Cited

U.S. PATENT DOCUMENTS

| | | |
|---|---|---|
| 3,343,421 | 9/1967 | Miller .................... 73/864.34 |
| 3,457,787 | 7/1969 | Maatsch et al. ............ 73/863.24 |
| 3,653,265 | 4/1972 | Vallino et al. ............ 73/863.83 |
| 3,793,886 | 2/1974 | Rosenwald . |
| 3,920,397 | 11/1975 | Small et al. ............. 73/61.52 |
| 3,973,440 | 8/1976 | Vande Ven et al. .......... 73/863.81 |
| 4,116,837 | 9/1978 | Biermacher . |
| 4,980,296 | 12/1990 | Trisciani et al. .......... 73/864.35 |
| 5,098,847 | 3/1992 | Welker . |
| 5,265,483 | 11/1993 | Farrell et al. . |
| 5,358,639 | 10/1994 | Yasuda et al. . |

FOREIGN PATENT DOCUMENTS 0 405 475 A2   1/1991   European Pat. Off. .

*Primary Examiner*—Robert Raevis
*Attorney, Agent, or Firm*—Reid S. Willis

[57] ABSTRACT

The present invention is a self-contained apparatus for sampling fluids. The apparatus permits a fixed volume of conditioned sample to be delivered directly or through a sample valve to a means of detecting the sample. The amount of sample that gets into the atmosphere is negligible since all or all but a minuscule amount of the sample is returned to the vessel. Sample handling and maintenance are minimized, and calibration of analytical instrumentation is simplified.

7 Claims, 3 Drawing Sheets

SELF-CONTAINED ON-LINE SAMPLING APPARATUS

CROSS REFERENCE TO RELATED APPLICATION

This application claims the benefit of U.S. provisional application Ser. No. 60/007,476, filed Nov. 22, 1995.

BACKGROUND OF THE INVENTION

The present invention is a self-contained on-line sampling apparatus that eliminates the venting of unused sample into the atmosphere.

On-line analysis of process streams is used for a variety of reasons, including maintaining process control, preventing process upsets, improving product quality, increasing product throughput, and lowering costs of manufacturing. Current methods generally require that a sample be injected from a sample stream through a sampling valve and into an analytical instrument. If the sample is a gas or volatilizable liquid, the pressure fluctuations in the sample line can cause differences in the amount of sample that is injected into the analytical instrument, thereby giving unreliable data. Pressure fluctuations can be controlled by trapping sample and venting excess into the atmosphere, but this is an undesirable alternative, since barometric pressure changes influence the precision of many analytical instruments. It would clearly be desirable to have an on-line sampling apparatus that provides for consistent sampling but which does not result in venting unused sample into the atmosphere. The present invention provides such a system.

DEFINITIONS

Figure 1:
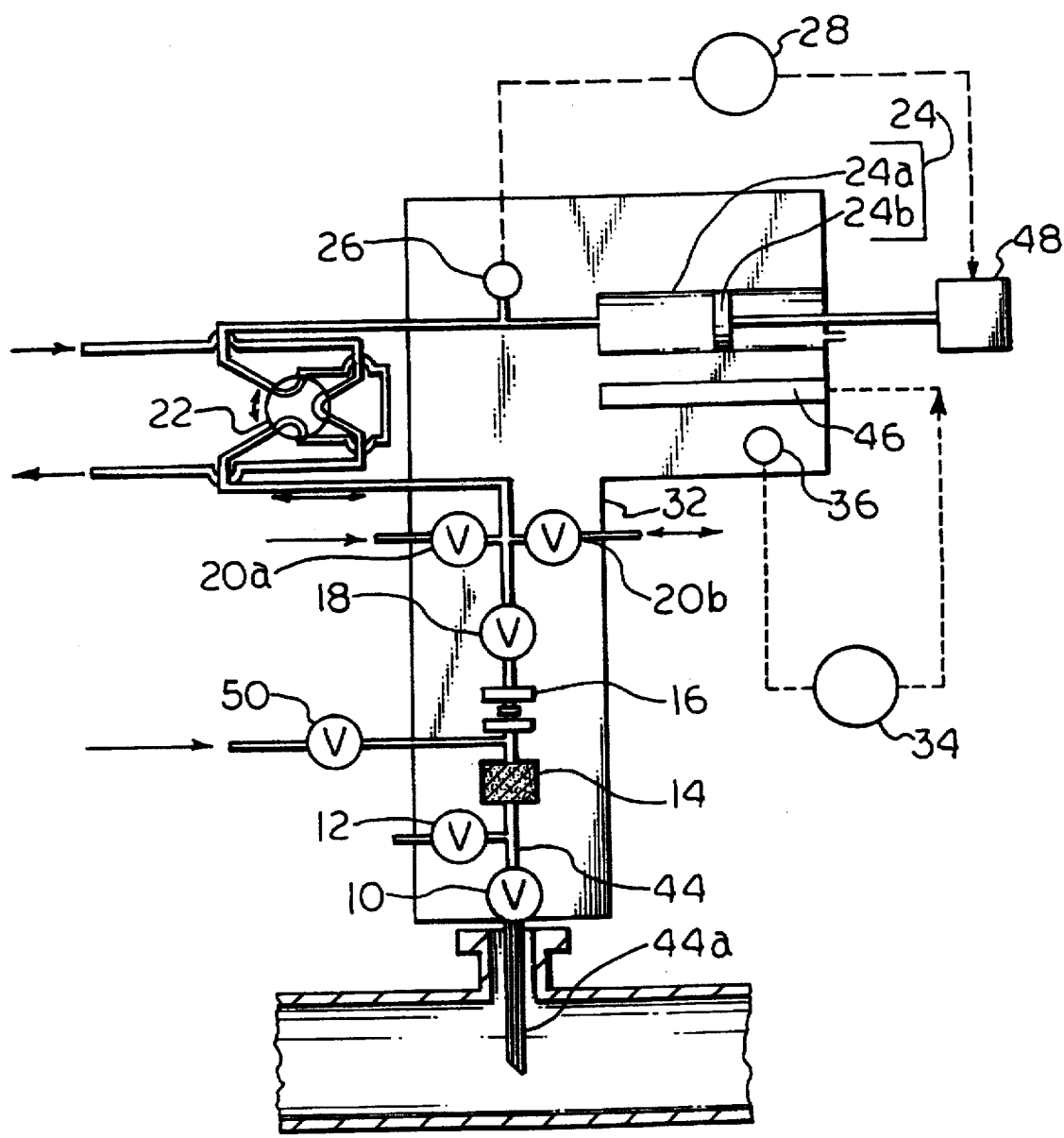
FIG. 1 is a schematic of a self-contained on-line sampling apparatus with sampling valve.

Auxiliary valve: An on/off flow control valve that a) directs flow to an analytical instrument outside of the main communication means, or b) allows collection of the reference fluid if desired. An auxiliary valve may also be used as a reference valve.

Bleed/Purge valve: An on/off flow control valve which allows a) depressurization and fluid removal when desired; b) introduction of purge fluid, which is an external purge gas or solvent, for cleaning the apparatus; c) a means for introducing an external fluid into the vessel; or d) withdrawal of fluid for assay at a remote site. This valve is set in a normally closed position.

Block valve: An on/off valve, typically 2-port, that serves as a) a means of allowing fluid passage into the variable volume device and b) a means of isolating a sample of fluid from the vessel. The block valve is preferably controllable by pneumatic actuation, but other actuation means such as electric or hydraulic actuation could be used.

Coupler: A fitting that allows for facile disconnection and reconnection of parts of the apparatus from the vessel.

Filter: Any means of impeding the passage of solid particulates in a flowing stream from upstream of the means to downstream of the means.

Fluid communicating means: A means by which fluid is transferred from a sample source to a variable volume device. The means is usually a sample line or a series of sample lines, but may also include a sample probe inserted into the sample source.

Isolation valve: An on/off valve proximal to the vessel and in direct communication with the fluid. This valve is set in a normally open position.

Manifold: A body suitable for internally routing fluid communicating means and for mounting valves, filter, variable volume device, etc.

Pressure controller: A device in electrical or mechanical communication with the pressure sensor and the variable volume device that controls pressure by causing the fluid in the variable volume device to expand or compress.

Pressure sensor: A device that measures pressure.

Reference valve: An on/off valve, typically 2-port, that is used to introduce reference fluids for zero, span, calibration, benchmarking, or standardization of an analytical instrument, detector, sensor, or apparatus.

Sample probe: A tube through which sample from the vessel passes into the apparatus, and ultimately into an analytical instrument. The sample probe is also part of the fluid communicating means.

Sampling valve: A valve designed to transfer a fixed volume of sample into an analytical instrument.

Self-purge valve: An optional on/off valve, typically 2-port, that can be used to automatically introduce a flushing, cleaning fluid into the apparatus to backflush the filter. This valve is useful when the process fluid contains entrained solid particulates that may collect on the filter.

Temperature controller: A device in electrical, pneumatic, or mechanical communication with the temperature sensor and a heating/cooling control device that controls the temperature of the manifold.

Temperature sensor: A device that measures temperature.

Variable volume device: A device with controllable volume, for example, a reciprocating piston in a chamber.

Vessel: The sample source.

DETAILED DESCRIPTION OF THE INVENTION

In one aspect, the self-contained on-line sampling apparatus of the present invention comprises an isolation valve, a block valve, a sampling valve, and a variable volume device, all connected in series and all in fluid communication with one another. A pressure sensor is also in fluid communication with the above-listed elements. A pressure controller is in operative communication with the variable volume device and the pressure sensor, preferably by way of closed-loop feedback control between the pressure sensor and the variable volume device. In some instances, for example, where the analytical instrument is an infrared, Raman, or UV/VIS spectrometer, the sampling valve may not be necessary.

Referring to FIG. 1, which represents a schematic of a preferred embodiment of the present invention, the self-contained on-line sampling apparatus comprises an isolation valve (10), a bleed/purge valve (12), a flow-through filter (14), optionally a self-purge valve (50), which preferably has 2-ports, a coupler (16), a block valve (18), a reference valve (20a), and optionally an auxiliary valve (20b), which preferably has 2-ports, a sampling valve (22), and a variable volume device (24) having a chamber (24a) and a reciprocating piston (24b), all in fluid communication and connected in series by way of a fluid communicating means (44), which extends from the tip of a sample probe (44a) to the variable volume device (24), but which does not include the variable volume device (24). As defined herein, the term "connected in series" means that the elements are situated in the order stated. However, it is not necessary that fluid pass through every element. For example, as FIG. 1 shows, fluid from the sample source does not ordinarily pass through the bleed/purge valve (12), the reference valve (20a), the optional auxiliary valve (20b), or the optional self-purge valve (50). A pressure controller (28) controls the pressure in the variable volume device (24) through closed-loop feedback control with a pressure sensor (26), an actuator (48), and the piston (24b) of the variable volume device (24).

The elements of the apparatus are all preferably mounted on a manifold (32), which can be maintained at a specified temperature by a temperature controller (34), which is in electrical, pneumatic, or mechanical communication with a temperature sensor (36) and a heating/cooling device (46), which is preferably a heating cartridge or a vortex cooler or a thermoelectric cooler. The total volume available for sample in the fluid communicating means (44) is less than the maximum volume available for sample in the variable volume device (24). More preferably, the ratio of the maximum volume available for sample in the variable volume device (24) to the total volume available for sample in the fluid communicating means (44) is at least about 2:1, more preferably at least about 5:1, and most preferably at least about 10:1, and preferably not greater than 100:1. The fluid communicating means (44) is preferably one or more sample tubes that have an inner diameter in the range of from about 0.010" to about 0.055".

Again referring to FIG. 1, the sampling apparatus is advantageously operated in the presence of a reference fluid in the following manner. With the isolation valve (10) in the "open" position, the bleed/purge valve (12) in the "closed" position, and the optional self-purge valve (50) actuated to the "closed" position, the reference valve (20a) is actuated to the "open" position and the piston (24b) is retracted so that fresh reference fluid from the reference source (not shown) is drawn into the variable volume device chamber (24a). During extension of the piston (24b), the reference valve (20a) is actuated "closed" while the block valve (18) is actuated "open" allowing reference fluid to pass into the vessel. Alternatively, if the reference fluid requires collection, auxiliary valve (20b) is actuated "open" during the piston extension. One retraction/extension of the piston (24b) is referred to as a cycle. This retraction/extension cycle can be automatically set for a fixed number of times. The block valve (18) (or, alternatively, the auxiliary valve (20b)) and the reference valve (20a) are then actuated to the "closed" position (if not already in the "closed" position) so that a sample of the reference fluid is isolated between the block valve (18) and the piston (24b). The desired pressure in the closed system is obtained by automatic manipulation of the volume in the variable volume device (24), typically by actuation of the piston (24b), which is in operative communication with the closed-loop pressure controller (28). When the desired pressure is obtained, a sample from the sampling valve (22) is injected into a carrier fluid stream, which carries the sample to an analytical instrument, which may be situated near to or remotely from the sampling apparatus. After injection, the block valve (18) is advantageously reopened so that sample from the variable volume device (24) can be flushed back into the vessel. Alternatively, the auxiliary valve (20b) can be reopened to collect the reference sample. The system is flushed, preferably at least three times, before a fresh sample is injected into the analytical instrument. The reference fluid is preferably a gas or a volatilizable liquid.

Figure 2:
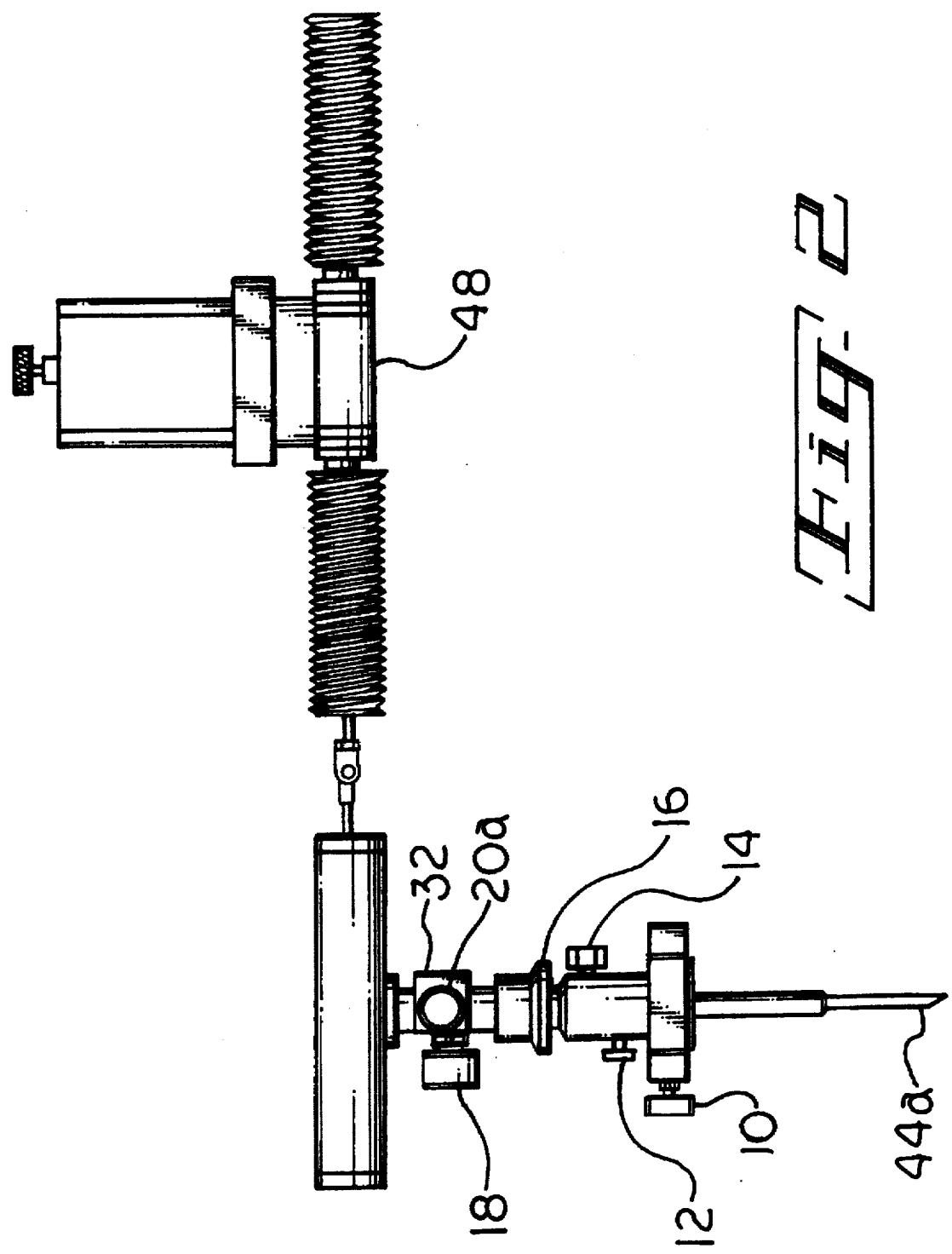
FIG. 2 is a side view of the sampling apparatus.

The isolation valve (10) functions as a means of isolating the sampling apparatus from the vessel. Such means include, but are not restricted to a plug valve, a gate valve, a needle valve, a ball valve, or a pinch valve. Actuation of the isolation valve (10) is typically done manually, but automatic means such as hydraulic, pneumatic, or electrical actuation can also be used. The isolation valve (10) preferably includes a sample probe (44a) which is a tube inserted into the vessel through which sample passes from the vessel to the fluid communicating means (44). A preferred isolation valve (10) is a flange isolation valve as depicted in FIG. 2.

Figure 3:
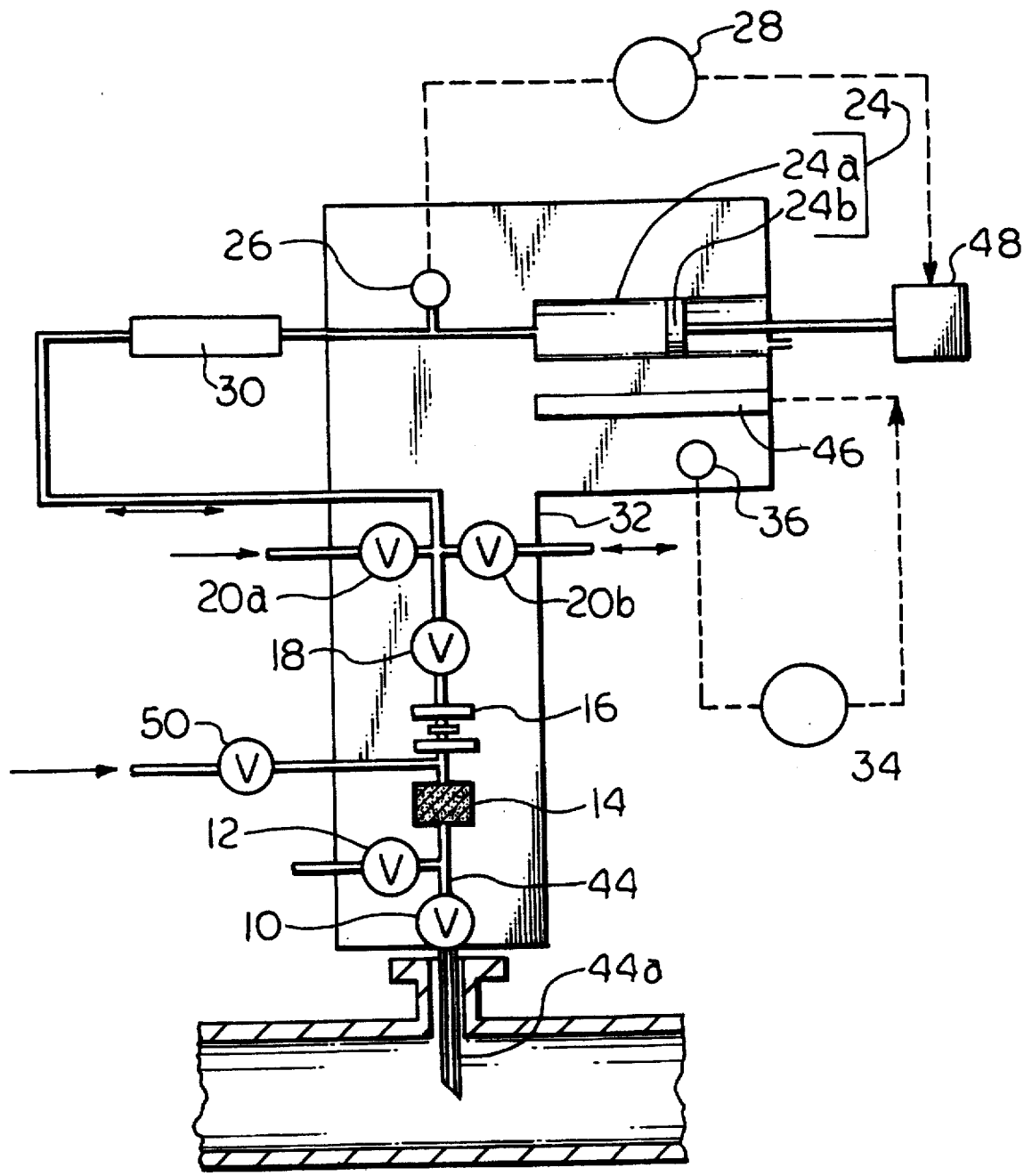
FIG. 3 is a schematic of a self-contained on-line sampling apparatus that includes a sample cell for an analytical instrument and no sampling valve.

Referring to FIG. 3, which represents another preferred embodiment of the invention, the isolation valve (10), the bleed/purge valve (12), the flow-through filter (14), optionally the self-purge valve (50), the coupler (16), the block valve (18), the reference valve (20a), optionally the auxiliary valve (20b), a sample cell (30) for a light sensing analytical instrument such as an infrared, Raman, or UV/VIS spectrometer, and the variable volume device (24), are all connected in series and all in fluid communication. As in FIG. 1, the pressure sensor (26) is in fluid communication with the above-named elements. The manifold (32), the temperature controller (34), the temperature sensor (36), and the heating/cooling device (46) are also present in this alternative embodiment. The sampling valve (22) shown in FIG. 1 need not be present. Referring to FIG. 1 and FIG. 3, the preferred embodiment of the apparatus of the present invention includes a bleed/purge valve (12) in fluid communication with the isolation valve (10). The bleed/purge valve (12) can provide several functions including means for: a) depressurizing the sample line to facilitate maintenance of the apparatus (for example, filter replacement and trouble-shooting); b) introducing an external purge fluid such as nitrogen or a suitable solvent to clean the apparatus; c) introducing an external purge fluid into the vessel; and d) withdrawing and collecting fluid for remote assay.

The flow-through filter (14) is preferably self-cleaning by the back flushing action of the variable volume device (24). Since only small amounts of sample are filtered for each analyzed sample, filter changes are minimized. Preferred flow-through filters include sintered metal, or wire mesh style filters. A sintered metal filter manufactured, for example, by Newmet Krebsoge is especially preferred. The optional self-purge valve (50) is useful in allowing a continuous flow of cleansing purge fluid backflowing through the filter during the time when sampling is not occurring. This feature is useful if the vessel contents contain a sufficient amount of entrained solids to plug the filter. The self-purge valve (50) is preferably a miniature solenoid valve, manufactured, for example, by Parker Hannifin Corporation General Valve Division. The sampling valve (22) is preferably used to inject a fixed volume of sample into a gas chromatograph or a mass spectrometer. The sampling valve (22) is preferably a 6-port sampling valve with a fixed sampling loop, manufactured, for example, by Valco Instrument Co. Inc. or ABB/Process Analytics, Inc. The variable volume device (24) is preferably a reciprocating piston in a syringe-like device in operative communication with the pressure sensor (26) and the pressure controller (28).

An example of a preferred pressure sensor (26), which is preferably an absolute pressure measuring device, is a semiconductor strain gauge transducer manufactured, for example, by Entran Devices, Inc. A preferred pressure controller (28) or temperature controller (34) is a programmable controller, for example, a programmable logic controller manufactured by AEG/Modicon, Inc. A preferred block valve (18), reference valve (20a), or optional auxiliary valve (20b) is a springless diaphragm valve, manufactured, for example, by Nupro Co. A plurality of reference valves may be used to introduce reference fluids for zero, span, calibration, benchmarking, or standardization of an analytical instrument, detector, or sensor.

A preferred actuator (48) suitable for the variable volume device (24) is a stepper motor actuator, manufactured, for example, by Jordan Controls, Inc. A preferred temperature sensor (36) is a resistance temperature detector (RTD). A preferred control system for automatically operating and synchronizing all sampling apparatus valves and operative equipment is an AEG/Modicon, Inc. programmable logic controller.

In a preferred method of the present invention (referring to FIG. 1), the isolation valve (10) is in the "open" position, the bleed/purge valve (12) is in the "closed" position, the optional self-purge valve (50) is actuated to the "closed" position, the block valve (18) is actuated to the "open" position and the piston (24b) is cycled so that fresh sample from the vessel is drawn into the variable volume device chamber (24a). The block valve (18) is then actuated to the "closed" position so that the sample is isolated between the block valve (18) and the piston (24b). The desired pressure in the closed system is obtained by automatic manipulation of the volume in the variable volume device (24) typically by actuation of the piston (24b), which is in operative communication with the closed-loop pressure controller (28). When the desired pressure is obtained, a sample from the sampling valve is injected into a carrier fluid stream, which transports the sample to an analytical instrument. After injection, the block valve (18) is advantageously reopened so that sample from the variable volume device (24) can be flushed back into the vessel. The system is preferably flushed at least three times before a fresh sample from the vessel is injected into the analytical instrument. The analytical instrument can be, for example, a gas chromatograph, a mass spectrometer, an infrared spectrometer, Raman spectrometer, a UV/VIS spectrometer, a paramagnetic oxygen analyzer, or a thermal conductivity analyzer. The sample fluid is preferably a gas or a volatilizable liquid.

In another preferred method of the present invention (referring to FIG. 3), the isolation valve (10) and the block valve (18) are actuated to the "open" position and the variable volume device (24) is cycled so that fresh sample from the vessel is drawn into the cell (30) for an infrared, Raman, or UV/VIS spectrometer. The block valve (18) is then actuated to the "closed" position so that the sample is isolated between the block valve (18) and the variable volume device (24). The desired pressure in the closed system is obtained by automatic manipulation of the volume in the variable volume device (24) by actuation of the piston (24b), which is in operative communication with the pressure controller (28). When the desired pressure is obtained the UV/VIS, Raman, or infrared spectrometer records a spectrum. The block valve (18) is advantageously reopened so that sample from the variable volume device (24) can be flushed back into the vessel. The system is preferably flushed at least three times before a spectrum of the sample in the cell (30) is recorded. The sample fluid is preferably a gas.

The apparatus of the present invention allows for a fixed volume of conditioned sample to be delivered directly, or through a sample valve, to a means of detecting the sample. The amount of sample that gets into the atmosphere is negligible since all or all but a minuscule amount of the sample is returned to the vessel. Sample handling and maintenance are minimized, precision is enhanced, and analytical instrument calibration is simplified. Typically, no external pumps or process sample vent return systems are required.

What is claimed is:

1. A self-contained on-line sampling apparatus comprising:

a) an isolation valve;

b) a block valve;

c) a sampling valve; and d) a variable volume device having a chamber and a reciprocating piston;

wherein the isolation valve, the block valve, the sampling valve, and the variable volume device are all connected in series and in fluid communication with one another by a fluid communicating means, the apparatus further comprising;

e) a pressure sensor which is in fluid communication with elements a to d;

f) a pressure controller in operative communication with the pressure sensor and the variable volume device; and g) a flow-through filter in fluid communication with the isolation valve, the block valve, the sampling valve, the variable volume device, and the pressure sensor, the flow-through filter being situated between the isolation valve and the block valve.

2. The self-contained on-line apparatus of claim 1 wherein the fluid communicating means includes a sample probe that is connected to the isolation valve and is insertable into a process stream.

3. The self-contained on-line apparatus of claim 2 wherein the ratio of the volume available for a sample in the variable volume device to the volume available for a sample in the fluid communicating means is at least about 2:1.

4. The self-contained apparatus of claim 1 further comprising a bleed/purge valve in fluid communication with the isolation valve, the block valve, the sampling valve, the variable volume device, the pressure sensor, and the flow-through filter, the bleed/purge valve being situated between the filter and the isolation valve.

5. The self-contained apparatus of claim 4 further comprising a reference valve in fluid communication with the isolation valve, the block valve, the sampling valve, the variable volume device, the pressure sensor, the flow-through filter, and the bleed/purge valve, the reference valve being situated between the block valve and the sampling valve.

6. The self-contained apparatus of claim 5 further comprising a coupler situated in fluid communication with the isolation valve, the block valve, the sampling valve, the variable volume device, the pressure sensor, the flow-through filter, the bleed/purge valve, and the reference valve, the coupler being situated between and the flow-through filter and the block valve.

7. The self-contained apparatus of claim 6 further comprising a self-purge valve situated between the coupler and the flow-through filter.

\* \* \* \* \*